United States Patent [19]
Kawand

[11] Patent Number: 5,685,858
[45] Date of Patent: Nov. 11, 1997

[54] SLIDABLE SEAL FOR USE WITH A CATHETER GARD UNIT

[75] Inventor: John George Kawand, Clifton, N.J.

[73] Assignee: Datascope Corp., Montvale, N.J.

[21] Appl. No.: 435,945

[22] Filed: May 17, 1995

[51] Int. Cl.[6] ..................... A61M 5/00
[52] U.S. Cl. ............ 604/171; 604/167; 604/178; 604/243; 604/283
[58] Field of Search ............ 604/105–117, 164–167, 604/171, 240–243, 280–283, 178

[56] References Cited

U.S. PATENT DOCUMENTS

| | | | |
|---|---|---|---|
| 4,235,232 | 11/1980 | Spaven | 128/214.4 |
| 4,473,067 | 9/1984 | Schiff | 128/1 |
| 4,826,477 | 5/1989 | Adams | 604/4 |
| 4,840,613 | 6/1989 | Balbierz | 604/51 |
| 4,929,236 | 5/1990 | Sampson | 604/175 |
| 4,969,879 | 11/1990 | Lichte | 604/283 |
| 5,057,084 | 10/1991 | Ensminger | 604/167 |
| 5,242,414 | 9/1993 | Fischell | 604/168 |
| 5,242,431 | 9/1993 | Kristiansen | 604/283 |
| 5,295,658 | 3/1994 | Atkinson | 251/149.1 |
| 5,312,377 | 5/1994 | Dalton | 604/283 |
| 5,322,518 | 6/1994 | Schneider | 604/247 |
| 5,342,316 | 8/1994 | Wallace | 604/167 |
| 5,429,619 | 7/1995 | Furnish | 604/283 |

Primary Examiner—Sam Rimell
Assistant Examiner—Robert V. Racunas
Attorney, Agent, or Firm—J. Gary Mohr

[57] ABSTRACT

A catheter gard unit is disclosed herein which includes a flexible tapered introduction guide. The distal end of the tapered introduction guide, in a sheath procedure, is placed over a guide wire and into a sheath, both of which have been pre-placed within a patient's body. In a sheathless procedure, the distal end of the tapered introduction guide is placed adjacent the skin of the patient and over the pre-placed guide wire. The gard unit comprises a body with a passageway therethrough for the passage of the catheter tube. A resilient slidable seal is mounted upon the tapered introduction guide of the gard unit. The slidable seal is adapted to slid over and seal the connection between the introduction guide, through which the catheter is placed, and a hemostasis valve of the sheath, after insertion of the sheath into the patient's body and thereby form a liquid seal between the introduction guide and the sheath. Thus, in use, liquid is prevented from leaking between the sheath and the catheter gard unit at the point of connection. When a sheathless procedure is performed the slidable seal is positioned and retained on the catheter gard unit removed from the point where the introduction guide meets with the skin of the patient.

5 Claims, 4 Drawing Sheets

SLIDABLE SEAL FOR USE WITH A CATHETER GARD UNIT

FIELD OF THE INVENTION

The present invention relates to a catheter gard unit for preventing liquid leakage, and more particularly, concerns a slidable seal suitable For use with a catheter gard unit used in conjunction with a catheter tube for insertion into a patient's body during a sheathed or sheathless procedure. The slidable seal being particularly useful in preventing blood from leaking from the connecting junction of the catheter gard unit with the sheath or extension thereof.

BACKGROUND OF THE INVENTION

Catheter guard units are employed for a variety of purposes, including the administration of liquids into the bloodstream, monitoring the central venous pressure, placement of intra-aortic balloons and the like. Many known techniques for utilizing a catheter guard unit are described in U.S. Pat. No. 4,235,232 assigned to Johnson & Johnson. All of said devices try to solve the problem of undesirable leakage between the catheter tube and the sheath, but none disclose a simple device that provides an effective unitary sealing unit that is easy to use, provides improved strain relief and eliminates potential leak sites.

An object of the present invention is therefore to provide an effective unitary sealing unit that is easy to manufacture, cost effective, easy to use and provides both improved stain relief and elimination of potential leak sites.

SUMMARY OF THE INVENTION

From a structural standpoint, the slidable sealing device of the present invention is notably different from the prior art sealing devices used in conjunction with catheter gard units for the placement of a catheter tube into the bloodstream or other body liquid conduits. For instance, the present slidable seal is a one-piece device, i.e., the resilient sealing portion and the body portion are both integrally formed into a unitary structure that is easily insertable in only one direction over the introduction guide. This offers the advantages of simplicity of assembly, in-expensive manufacture, functional conveniences and reduction of the total number of potential leaks sites. Moreover, the present slidable seal, in addition to providing an effective liquid seal, also serve to maintain the catheter gard unit in position, offers improved strain relief of the introduction guide and prevent excessive longitudinal movement while still allowing for rotational movement of the catheter gard unit in relation to the sheath. Further, since the seal is slidable on the catheter gard unit it can easily be slid into or out of a sealing position for sheath and sheathless procedures. Other advantages and benefits of the present invention are provided as well.

DETAILED DESCRIPTION OF THE INVENTION

Figure 1:
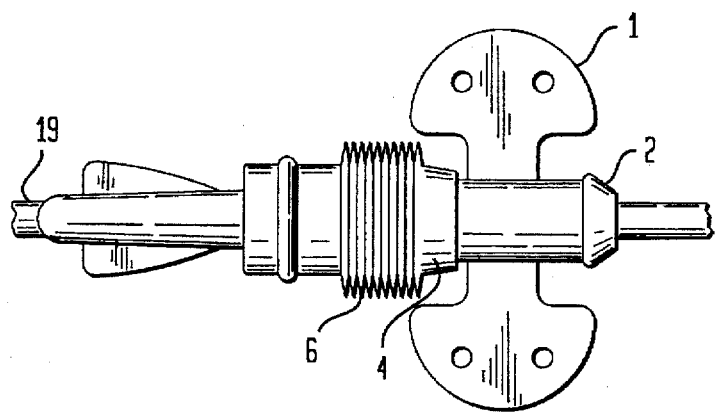
FIG. 1 is a side view of a catheter gard unit with a prior art bellows sealing unit in a retracted position.

While this invention is satisfied by embodiments in many different forms, there is disclosed in the drawings and in the herein detailed preferred embodiment of the invention, what is to be considered as exemplary of the principles of the invention. This illustrated embodiment, however, is not to limit the scope of the invention.

Figure 2:
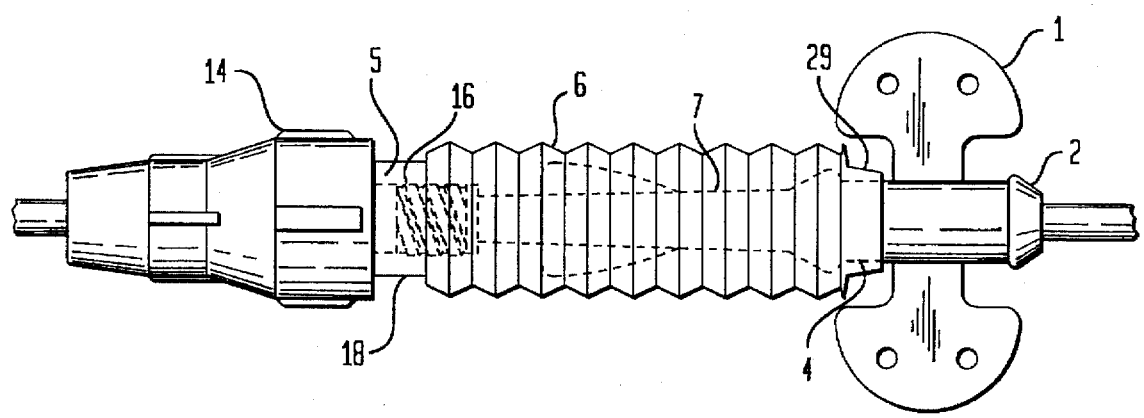
FIG. 2 is a side view of the catheter gard unit with the prior art bellows sealing unit in its expanded position and connected to a hemostasis valve.
Figure 3:
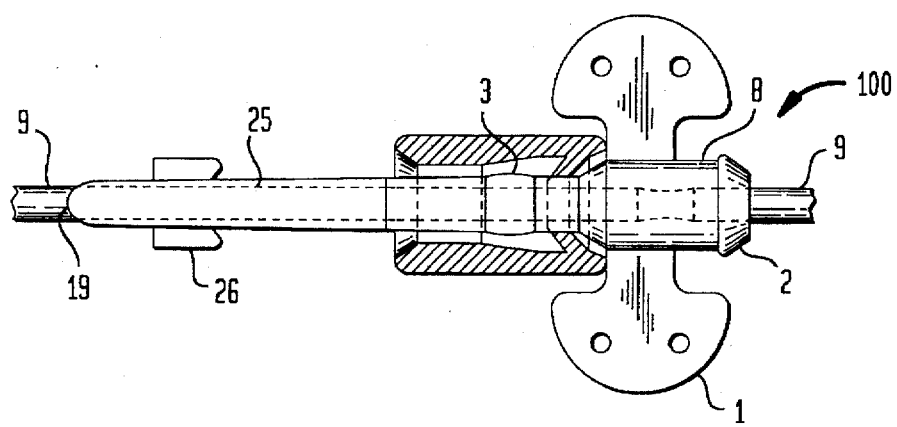
FIG. 3 is a top view of the catheter gard unit of the present invention with a slidable sealing unit in its non-sealing position for a sheathless procedure.
Figure 4:
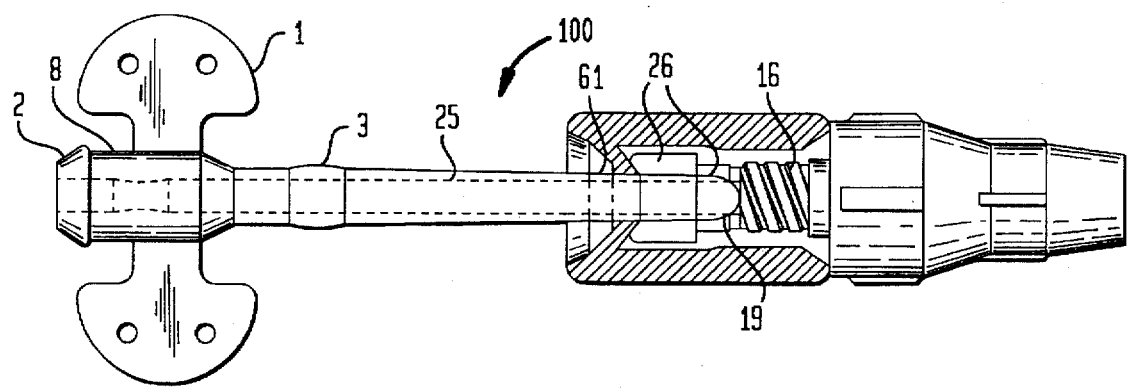
FIG. 4 is a top view of the catheter gard unit of the present invention with the slidable sealing unit in its sealing position for a sheath procedure.
Figure 7:
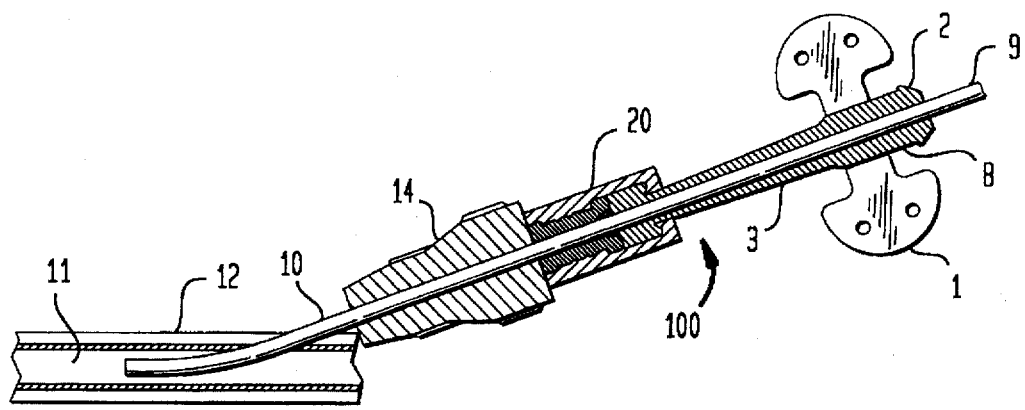
FIG. 7 is a side section view of the hemostasis valve, the sheath and catheter inserted into a patient's artery.

Turning now to the drawings and in particular FIGS. 3 and 4, there is illustrated a catheter gard unit 100 which is utilized in the delivery of a catheter 9 to a part of the human body such as an artery 11, see FIG. 7. Catheter gard unit 100 is comprised of a suture pad 1 for securing the gard unit 100 to the human body. At one end of suture pad 1 is a retainer 2, for use whenever an apparatus, as is known in the art, is to be attached to the catheter gard unit 100. At the other end of suture pad 1 is a seal retainer 4, Seal retainer 4, as shown in the prior art device, see FIGS. 1 and 2, retains a bellows sealing unit 6 to catheter gard unit 100. In the present invention there is no need for seal retainer 4, however, there is a snap ring 3, on a flexible tapered introduction guide 7, to maintain a slidable seal 20, as to be described later, removed from the point of catheter 9 insertion into a patient during a sheathless procedure. Adjacent to seal retainer 4 is the flexible tapered introduction guide 7, heretofore mentioned. Located between retainer 2 and seal retainer 4 is a barrel connector 8 that provides the mounting point for suture pad 1. Both tapered introduction guide 7 and barrel connector 8 contain a passageway 25 for the insertion of catheter 9 in a sliding sealing relation, as is known in the art, through tapered introduction guide 7 and barrel connector 8. In this manner the distal end of catheter 9 is positioned to be inserted into the human body while leaving the proximal end of catheter 9 available for attachment to an appropriate monitoring or pumping device, not shown, but with their attachment and use being as is known in the art. The positional relation of distal to proximal ends being, the distal end is considered the end closest to the point of initial insertion into the patient's body.

In operation, as can be seen in FIG. 7, sheath 10 is inserted into an artery 11 of patient 12. The flexible nature of sheath 10 assists in properly positioning the same in artery 11, while also minimizing any traumatic effects. Similarly, catheter 9 and tapered introduction guide 7 are also flexible for substantially the same reasons. Since tapered introduction guide 7 is flexible, precautions must be taken to prevent stress on guide 7 that would cause kinking of guide 7, near its distal thin end, or kinking of catheter 9 in the same location. Such stress relief will be discussed later. At the proximal end of sheath 10 is a hemostasis valve 14 which may be integral with or an extension of sheath 10. Hemostasis valve 14 has an internal tapered surface 15, see FIG. 6, which serves as a female connector for the tip 19 of introduction guide 7. The outer surface 16 of female connector 15 is either threaded or of such a shape or dimension, as is known in the art, to form an interference or snap fit with the resilient inner surface 17, of slidable seal 20, when slidable seal 20 is in its sealing position, see FIGS. 4 and 5. Since either an interference or snap fit is used, no indexing or special positioning is required between outer surface 16 and inner surface 17 in order to achieve a proper sealing connection at this sealing juncture. While this interference fit prevents, in a sheath procedure, blood leakage from between surfaces 16 and 17 it is still critical to prevent leakage between outer surface 61 of introduction guide 7 and inner surface 50 of slidable seal 20. Even though inner surface 50 of slidable seal 20 is in interference contact with introduction guide 7 all along the longitudinal dimension of guide 7, due to the need to move slidable seal 20 along guide 7, the interference contact can not be as great as would be needed to assure that no blood would leak between surfaces 50 and 61. This presents a dilemma as to how to seal the juncture between surfaces 50 and 61 while still allowing for a sliding relation between the two surfaces.

Figure 5:
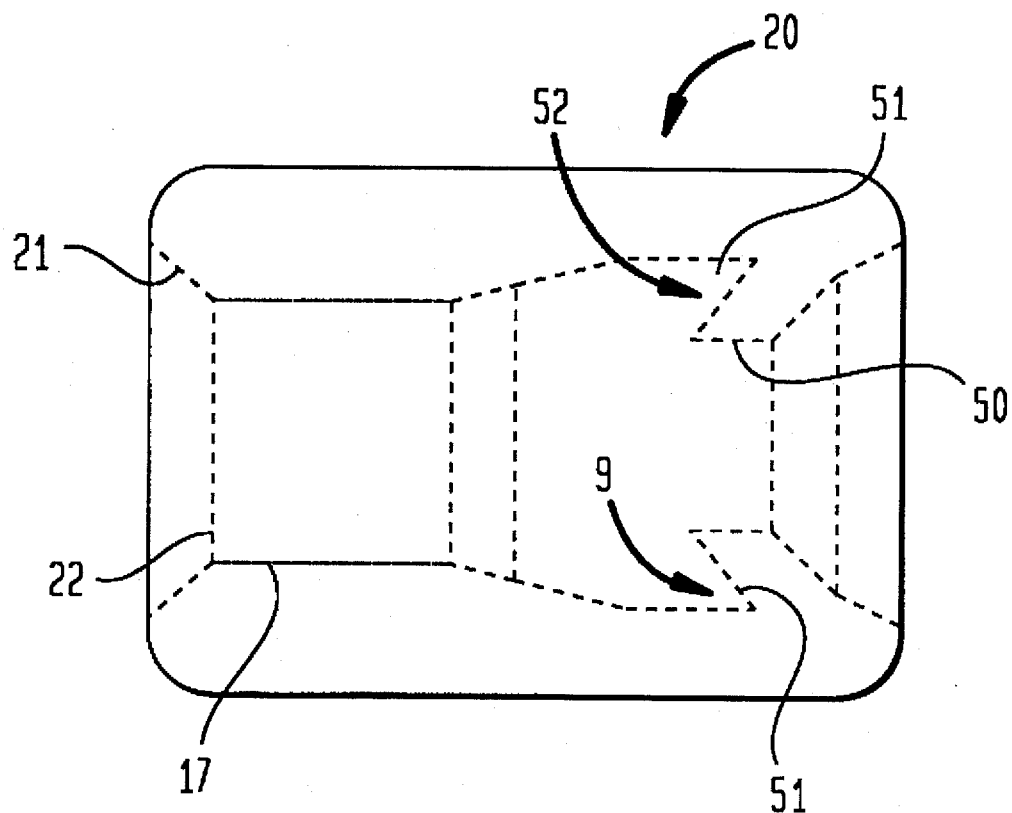
FIG. 5 is an enlarged side view of the slidable sealing unit of the catheter gard unit of the invention removed from the remaining portions of the catheter gard unit.
Figure 6:
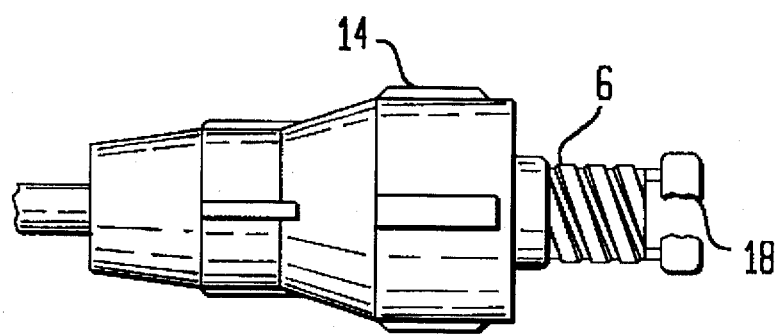
FIG. 6 is a side view of a hemostasis valve used with the catheter gard unit of the invention during a sheath procedure.

As can be seen from FIG. 5, the dilemma is solved by providing an undercut region 51 adjacent to inner surface 50 of slidable seal 20 to provide a cantilever effect to inner surface 50. This undercut region 51 provides inner surface 50 with the flexibility needed to allow guide 7 to be slid through inner surface 50 in both directions even though the diameter of inner surface 50 is less than that of the outer surface 61, see FIG. 8, of guide 7. In addition because of undercut region 51, the inner surface 50 of slidable seal 20 will close upon or form a seal with outer surface 61 of guide 7 whenever there is blood leakage. This is because the blood will tend to flow into pockets 52 created by undercut region 51 and thereby exert a force that pushes inner surface 50 closer and closer to outer surface 61 of guide 7 to provide a tighter and tighter seal between surface 50 and guide 7 as the leakage of blood increases and the need for a tighter seal becomes greater.

Under cut 51, coupled with a retaining device 26, hereinafter to be discussed, aides in the assembly of seat 20 on guide 7 by making it difficult for one to over come the interference of retaining device 26 with pockets 52 if one were to try to assembly slidable seal 20 incorrectly on guide 7. In the alternative, when one correctly assemblies seal 20 on guide 7, pockets 52 tend to collapse and thereby facilitate the movement of seal 20 over retaining devise 26, to be discussed later, for completing the assembly of seal 20 on guide 7.

Because slidable seal 20 is a unitary structure and more ridge than say bellows 6 of the prior art, slidable seal 20, when positioned over the thinner distal portion of flexible tapered guide 7, reinforces this thin portion of guide 7, which is vulnerable to kinking, and thereby aides in the prevention of kinking of both guide 7 and catheter 9. As to that portion of tapered guide 7 not reinforced by slidable seal 20, it is of a greater diameter and therefore better able, on its own, to resist kinking during a sheath procedure.

Figure 9:
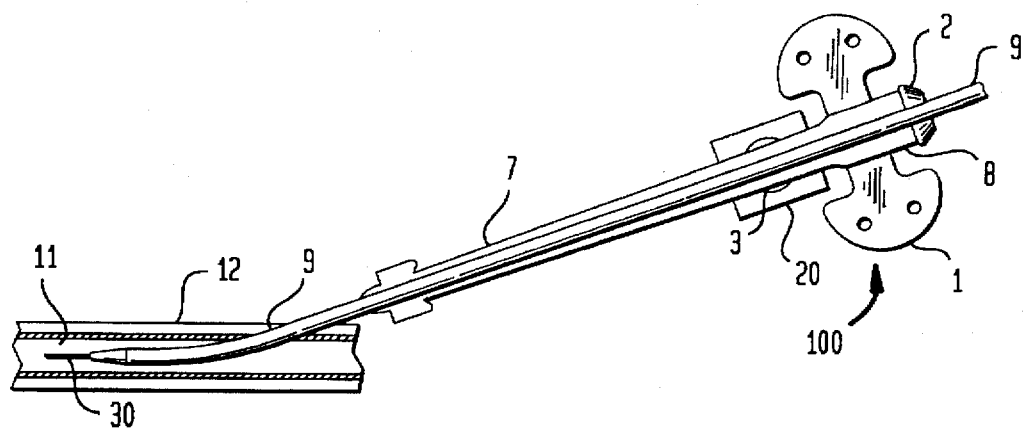
FIG. 9 is a side section view of the catheter gard unit of the invention inserted over the guide wire with the slidable sealing unit in its non-sealing position for a sheathless procedure.

In the sheathless application of catheter gard unit 100, slidable seal 20 is not needed and therefor there is a need to maintain it removed from the distal end of guide 7 as is shown in FIG. 9. This position is maintained by snap ring 3 having an outer diameter greater than that of inner surface 50. In this manner, once inner surface 50 is slid over snap ring 3 it will, by interference fit, remain removed from the tip 19 of guide 7 during the sheathless procedure where slidable seal 20 is not needed. Even with this interference fit, one can still easily slid inner surface 50 over the larger diameter snap ring 3, since undercut region 51 allows the diameter of inner surface 50 to increase as it is slid over ring 3.

Figure 8:
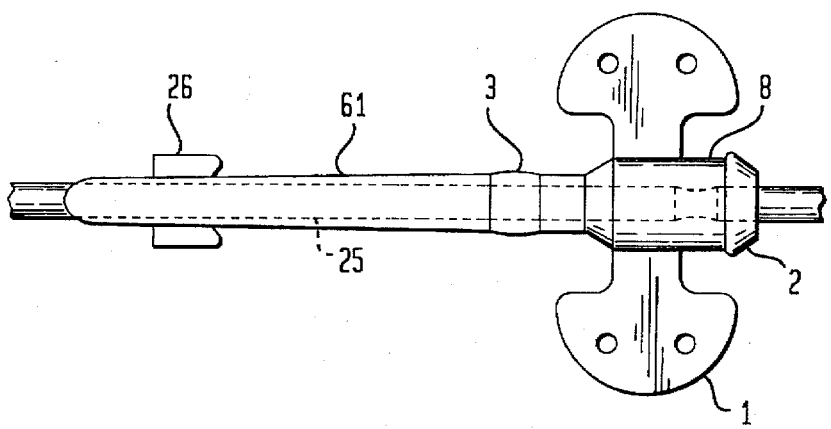
FIG. 8 is a side view of the catheter gard unit with the slidable sealer unit removed.

Slidable seal 20, as shown in FIG. 5, maybe formed of any known resilient material but dimensioned such that the circumference of inner surface 50 of slidable seal 20 is less than any portion of the outer circumference 61 of guide 7, see FIG. 8. This difference in circumference between the circumference of the outer surface 16 and the inner surface 50 is not so great as to make slidable seal 20 difficult to move longitudinally along guide 7, which movement is facilitated by the flexibility given to surface 50 by undercuts 51, but great enough that a liquid seal, created by blood flowing into pockets 52 behind surface 50 and forcing surface 50 toward surface 61 of guide 7, will be established that can withstand a pressure greater than that exerted by the blood of the human body. The distal end 21 of seal 20 is tapered such that the larger inner diameter 71 of slidable seal 20 is greater than the outer diameter of surface 16 of hemostasis valve 14 to aide in the location of slidable seal 20 over surface 16 of hemostasis valve 14. However the inner diameter 72 of slidable seal 20 is less than the outer diameter of surface 16 of hemostasis valve 14 thereby providing for a interference liquid seal between surfaces 17 and 16 when slidable seal 20 is positioned as shown in FIG. 4.

Since, in the present invention, sealing is accomplished by interference fit, no special indexing or positioning of seal 20 is required, in relation to the orientation of hemostasis valve 14, and therefore the ability to have rotational movement between sheath 10 and catheter gard unit 100 is maintained. This is unlike the prior art sealing devices in which the bellows 6 requires proper positioning or indexing and therefore precludes rotational movement between the sheath 10 and the catheter gard unit 100. In addition, since the slidable seal 20 is a unitary device it eliminates two potential leak sites of the prior art, namely the circumferential sealing of the bellows 6 about its two end points.

As to retaining device 26 located at the distal end of introduction guide 7, it may be formed in various shapes, such as wings, an annular flange or other known type of retaining shape. However, due to the structure of seal 20, retaining device 26 may now be of a sturdier construction than in prior art devices and thereby it is better suited to perform its various functions such as:

a. to maintain slidable seal 20 from being unintentionally removed from tapered introduction guide 7, but flexible enough as to not obstruct the insertion of slidable seal 20 over retaining device 26 when inserted in the proper direction onto introduction guide 7;

b. to provide a stop, in the sheath procedure, so that the user is assured that the distal tip of introduction guide 7 has been inserted into fitting 14 a sufficient depth to function properly and prevent slidable seal 20 from being removed from introduction guide 7 during this procedure, and c. to provide a stop, in a sheathless procedure, such that the distal end 27 of retaining device 26, may act as a block, upon reaching the skin of patient 12, see FIG. 9, and thereby aide the user in preventing the tip 19 of catheter gard unit 100 from being inserted too deeply into the patient 12 as the catheter gard unit 100 is being placed over the previously inserted guide wire.

While the invention has been described in connection with a specific embodiments thereof, it should be understood that it is capable of further modification, and this application is intended to cover any variations, uses, or adaptations of the invention following, in general, the principles of the invention and including such departures from the present disclosure as come within known or customary practice in the art to which the invention pertains and as may be applied to the essential features hereinbefore set forth, and as fall within the scope of the invention and the limits of the appended claims.

We claim:

1. A guard unit for connecting an external catheter to a sheath to prevent leakage of body fluids to the atmosphere, comprising:

an introduction guide;

a first end of the introduction guide for mating contact with the sheath;

a second end of the introduction guide for introduction of the external catheter;

a unitary resilient sealing means for sealing the first end of the introduction guide and the sheath from leakage of body fluids to the atmosphere, wherein the sealing means has a cantilevered projection about its inner circumference for maintaining the sealing means in sealing contact with the introduction guide and the cantilevered projection has an adjustment means to adjust its diameter wherein the adjustment means is comprised of a first circumferential surface of one diameter removed from the inner surface of the sealing means and a second circumferential surface of a greater diameter attached to the inner surface of the sealing means; and the sealing means having a means for providing an internal flexible diameter for maintaining the sealing means in slidable interference fit with the outer longitudinal surface of the introduction guide.

2. The introduction guide of claim 1 wherein the outer diameter of the introduction guide is tapered for mating with the inner diameter of the sheath.

3. The tapered introduction guide of claim 2 wherein a retaining means for retaining the sealing means from unintentional removal from the tapered introduction guide is located at the distal end of the tapered introduction guide.

4. The retaining means of claim 3 wherein a distal end of the retaining means provides a stop to aide in positioning the introduction guide.

5. The sealing means of claim 1 wherein the flexible diameter means further has means for adjusting its diameter upon fluid leaking into the sealing means.

* * * * *